(12) United States Patent
Barbut

(10) Patent No.: US 7,340,298 B1
(45) Date of Patent: Mar. 4, 2008

(54) ENHANCEMENT OF CEREBRAL BLOOD FLOW BY ELECTRICAL NERVE STIMULATION

(75) Inventor: Denise R. Barbut, Maple Grove, MN (US)

(73) Assignee: CoAxia, Inc., Maple Grove, MN (US)

( * ) Notice: Subject to any disclaimer, the term of this patent is extended or adjusted under 35 U.S.C. 154(b) by 384 days.

(21) Appl. No.: 10/655,353

(22) Filed: Sep. 3, 2003

(51) Int. Cl.
*A61N 1/18* (2006.01)

(52) U.S. Cl. .......................... 607/2; 607/117
(58) Field of Classification Search ............ 607/2, 607/117; 128/898, 899
See application file for complete search history.

(56) References Cited

U.S. PATENT DOCUMENTS

| | | | |
|---|---|---|---|
| 6,231,551 B1 | 5/2001 | Barbut | |
| 6,592,557 B2 | 7/2003 | Barbut | |
| 2003/0023200 A1 | 1/2003 | Barbut et al. | |
| 2004/0249429 A1* | 12/2004 | Tadlock | 607/116 |

FOREIGN PATENT DOCUMENTS

| | | |
|---|---|---|
| WO | WO 0051675 | 9/2000 |
| WO | WO 02085443 | 10/2002 |

OTHER PUBLICATIONS

Inoue, M., Nakase, H., Hirabayashi, H., Hoshida, T., Sakaki, T. "Effect of stimulation of the dorsal aspect of the cervical spinal cord on local cerebral blood flow and EEG in the cat." Neurological Research; Jun. 2000; 22(4): 386-392.*
Tuor, U.I., "Local Distribution of the Effects of Sympathetic Stimulation on Cerebral Blood Flow in the Rat", Brain Research, 529 (1990), pp. 224-231, Elsevier Science Publishers B.V. (Biomedical Division), U.S.

* cited by examiner

*Primary Examiner*—Angela D. Sykes
*Assistant Examiner*—Alyssa M. Alter
(74) *Attorney, Agent, or Firm*—O'Melveny & Myers LLP

(57) ABSTRACT

A method for increasing cerebral blood flow in a patient. A electrical stimulating device is provided. The electrical stimulating device is applied to the patient at a region adjacent the cervical sympathetic chain, the brain stem, the head, or the sympathetic nervous system. The electrical stimulating device is applied by any route selected from transcutaneous, subcutaneous, and subarachnoid. The electrical stimulating device is activated to stimulate or inhibit nerve impulses of the cervical sympathetic chain, thereby producing vasodilation in the cerebral vasculature, thereby increasing cerebral blood flow. Devices for increasing cerebral blood flow in a patient are also described.

7 Claims, 6 Drawing Sheets

ENHANCEMENT OF CEREBRAL BLOOD FLOW BY ELECTRICAL NERVE STIMULATION

FIELD OF THE INVENTION

The present invention relates to devices and methods for treating patients with focal cerebral ischemia such as acute ischemic stroke or vasospasm following subarachnoid hemorrhage or iatrogenic vasospasm, or global cerebral ischemia such as shock, dementia, or cardiac arrest, and other conditions of reduced cerebral perfusion, and more particularly to devices and methods that enhance cerebral blood flow in a patient by use of electrical stimulation to inhibit vascular regulation by the sympathetic nervous system.

BACKGROUND

Patients experiencing cerebral ischemia often suffer from disabilities ranging from dementia to transient focal neurological deficit to irreversible brain damage (stroke) or to death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., dementia, shock, cardiac failure, or cardiac arrest. Shock is the state in which failure of the circulatory system to maintain adequate cellular perfusion results in reduction of oxygen and nutrients to tissues. Within minutes of circulatory failure, tissues become ischemic, particularly in the heart and brain.

The two common forms of shock are cardiogenic shock, which results from severe depression of cardiac performance, and hemorrhagic shock, which results from trauma. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, and acutely acquired ventricular septal defects, can also cause cardiogenic shock by reducing cardiac output. Additional causes of cardiogenic shock include cardiac arrhythmia, such as ventricular fibrillation. Hemorrhagic shock is typically the result of penetrating injuries caused by, for example, traffic accidents and gunshot wounds. In this case, cardiac function is unimpaired and the cause of shock is circulatory blood loss.

Treatment of global cerebral ischemia involves treating the source of the systemic circulatory failure and ensuring adequate perfusion to the central nervous system. For example, treatment of cardiogenic shock due to prolonged cardiopulmonary bypass consists of cardiovascular support with the combination of inotropic agents such as dopamine, dobutamine, and intra-aortic balloon counterpulsation. Treatment of hemorrhagic shock consists of volume replacement and hemostasis. When these measures fail, supracoeliac aortic clamping is used. Vasoconstrictors, such as norepinephrine, are also administered systemically to maintain systolic blood pressure (ideally above 80 mmHg). Unfortunately, these agents produce pressure at the expense of flow, particularly blood flow to small vessels such as the renal arteries. The use of the vasoconstrictors is, therefore, associated with significant side effects, such as acute renal failure, congestive heart failure, and cardiac arrhythmias.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system. Stroke is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time because some thrombi get absorbed into the circulation, or fragment and travel distally over a period of a few days. In June 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

In both global and focal ischemia, patients develop neurologic deficits due to the reduction in cerebral blood flow. One treatment may include the use of devices to increase blood flow to the cerebral vasculature as the sole therapy. Alternatively, treatments include measures to increase blood flow to the cerebral vasculature to maintain viability of neural tissue, thereby increasing the length of time available for any adjunct interventional treatment and minimizing neurologic deficit while waiting for resolution of the ischemia. Augmenting blood flow to the cerebral vasculature is not only useful in treating occlusive or vasospastic cerebral ischemia, but may also be useful during interventional procedures, such as carotid angioplasty, stenting or endarterectomy, which might otherwise result in focal cerebral ischemia with or without focal vasospasm, and also cardiac procedures which may result in cerebral ischemia, such as cardiac catheterization, electrophysiologic studies, and angioplasty, and also chronic conditions associated with poor perfusion such as dementia.

New devices and methods are thus needed for augmentation of cerebral blood flow in treating patients with either global or focal ischemia caused by reduced perfusion, thereby minimizing neurologic deficit and improving cognition.

SUMMARY OF THE INVENTION

The present invention relates to methods for increasing cerebral blood flow in a patient. The sympathetic and parasympathetic nervous systems operate in a delicate balance to regulate vascular tone and thereby control cerebral blood flow. The activation of the parasympathetic nervous system generally promotes vasodilatation, whereas the activation of the sympathetic nervous system generally promotes vasoconstriction. The parasympathetic and the sympathetic nervous systems therefore compete to achieve the correct level of vasoregulation. The level of vasoregulation that results from this competition is called the "basal tone."

The basal tone represents approximately 30% contribution from the sympathetic nervous system, and the remainder from the parasympathetic nervous system. The present invention is based on the surprising and unexpected discovery that vasodilatation and increased cerebral blood flow can be achieved by inhibiting the sympathetic contribution to vascular regulation. For example, by abolishing the sympathetic contribution to vascular regulation, a dilatation of at least 30% is achieved.

In a first example, an electrical stimulating device is provided. The electrical stimulating device may be a GRASS stimulator or any other suitable device. The electrical stimulating device is applied to the sympathetic nervous system. The electrical stimulating device may be applied to any of the cervical sympathetic chain, the stellate ganglion, the carotid body, the carotid bulb, the superior cervical ganglion, the middle cervical ganglion, and the inferior cervical ganglion. The electrical stimulating device may be applied by any method, including transcutaneous, or subcutaneous, e.g., posteriorly, at the level of C6, or anteriorly, medial, or lateral to the common carotid artery in the neck. In other cases, the electrical stimulating device is applied by epidural, subdural, subarachnoid probe (inserted through either the lumbar or cervical spine up to the level of C6 for close proximity to the ganglia), or direct contact with the ganglia. The electrical stimulating device is, in certain cases, applied to the transverse process of C6. In other cases, the electrical stimulating device is applied to the skin of the patient at a region 2 cm to the right of spinous processes of vertebral bodies C5-6. In still other cases, the electrical stimulating device is applied by intravascular, transmural access through the common carotid artery or other artery in the head or neck. A further approach is a cut down in the neck for direct positioning near the ganglion. Access may also be achieved by a transesophageal approach, with a probe positioned on the soft palate at the level of the pharynx to gain contact with the vagus nerve, the carotid body, and the cervical sympathetic chain.

In still other methods, the electrical stimulating device is operated to produce electrical stimulation comprising a pulse of 1 msec duration, 50 Hz, and 10 volts, with a stimulus train duration of 20 msec. In a further method, the electrical stimulating device is operated to produce electrical stimulation comprising a pulse of 0.1-3 msec duration, 25-75 Hz, and 5-15 volts, with a stimulus train duration of 10-30 msec.

The electrical stimulating device is then operated to inhibit nerve impulses of the sympathetic nervous system. The electrical stimulating device is operated in certain cases to produce electrical stimulation comprising a rectangular square pulse. The electrical stimulation produces vasodilation in the cerebral vasculature, thereby increasing cerebral blood flow. In other methods, the operator of the device will measure cerebral blood flow before and after the step of operating the electrical stimulating device. In still other methods, the operator will determine the increase in cerebral blood flow produced by operating the electrical stimulating device.

Blocking the ganglia will have an effect on cerebral blood flow through nerve endings or interconnecting nerves located on the carotid body, the common and internal carotid artery, the external carotid artery, the carotid siphon, and other intracranial and extracranial vessels all the way up to the pial and leptomeningeal vessels. The present invention will typically produce a 50% or more increase in cerebral blood flow, more preferably a 60% or more increase in cerebral blood flow, more preferably a 70% or more increase in cerebral blood flow, more preferably a 80% or more increase in cerebral blood flow, more preferably a 90% or more increase in cerebral blood flow. In the event that electrical stimulation or inhibition fails to produce a desired increase in cerebral blood flow, the $paCO_2$ level in the patient should be adjusted, and electrical stimulation or inhibition attempted again.

DETAILED DESCRIPTION

The autonomic nervous system that comprises of the parasympathetic and sympathetic nervous systems governs many bodily functions below the conscious levels. These functions include distribution of blood flow and the maintenance of tissue perfusion, and regulation of blood pressure. Changes to sympathetic and parasympathetic stimulation are frequently antagonistic and reciprocal, as exemplified by their opposing effects on vascular tone, thereby providing more precise control of the autonomic responses than by modulation of a single system.

Figure 1:
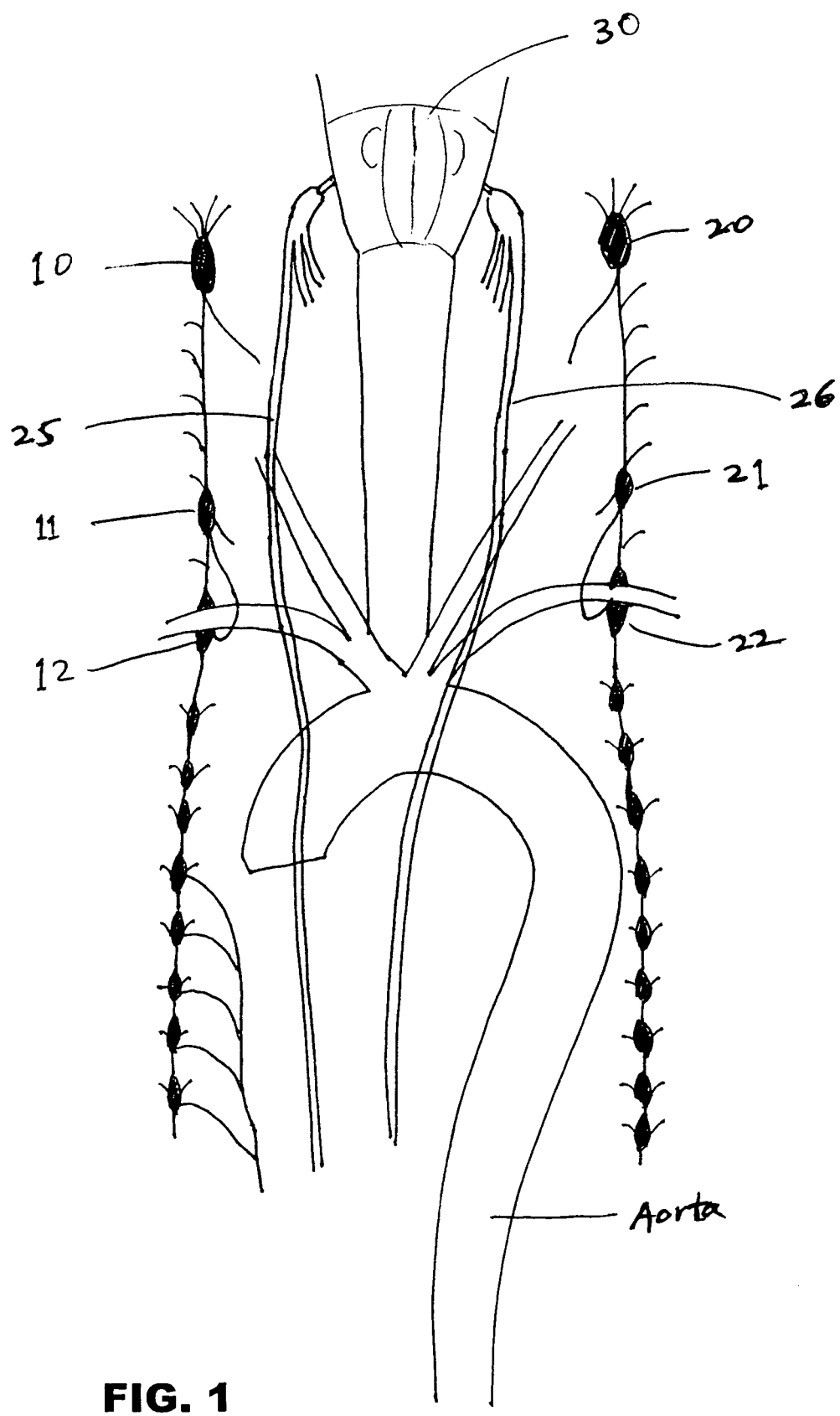
FIG. 1 depicts organization of the autonomic nervous system in the cervicothoracic region.

The organization of the sympathetic and the parasympathetic systems in the cervicothoracic region is shown in FIG. 1. Longitudinal strands of autonomic nerve fibers and their associated sympathetic ganglia are located in the neck anterolateral to the vertebral column from the level of the first cervical vertebra. The right cervical sympathetic trunk contains three sympathetic ganglia—right superior cervical ganglion 10, right middle cervical ganglion 11, and right inferior ganglion 12. Similarly, left cervical sympathetic trunk contains left superior cervical ganglion 20, left middle cervical ganglion 21, and left inferior ganglion 22. These ganglia receive their preganglionic fibers from the superior thoracic spinal nerves. Right superior cervical ganglion 10 sends its postganglionic branches to the external carotid artery and along the internal carotid artery into the cranial cavity. Right middle cervical ganglion 11 lies around the level of the cricoid cartilage, anterior to the vertebral artery. Right inferior cervical ganglion 12 lies at the level of the first rib and is usually fused with the first and/or thoracic ganglion to form a larger ganglion (known as the cervicothoracic or stellate ganglion).

Postganglionic fibers from right inferior cervical ganglion 12 innervate the heart and contribute to the vertebral plexus around the vertebral artery. The sympathetic trunk is closely regulated by the sympathetic centers located in brain stem 30. The brainstem sympathetic centers have an intrinsic activity of their own. Sympathetic outflow is initiated from the reticular formation of the medulla oblongata, pons, and certain areas or the hypothalamus. The parasympathetic system participates in the control of cardiovascular system by way of right vagus nerve 25 and left vagus nerve 26 that lies medial to the right and left cervical sympathetic chains, respectively.

Figure 2:
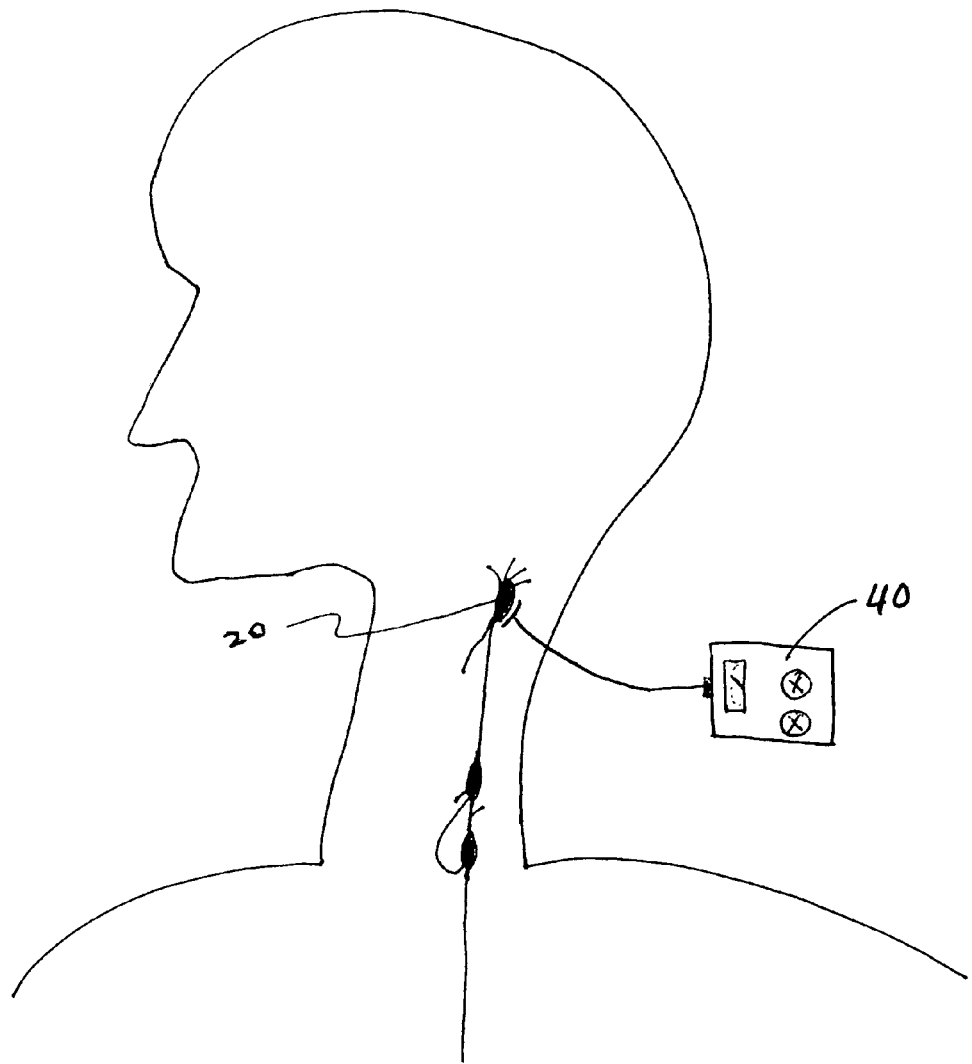
FIG. 2 depicts application of an electrical stimulation device to the left cervical sympathetic chain to produce cerebral vasodilation.

To increase cerebral blood flow in a stroke patient, a transcutaneous electrical stimulating device is applied to the skin of a patient at a region adjacent to the cervical sympathetic chain as shown in FIG. 2. Electrical stimulating device 40, such as a GRASS stimulator, is applied to the skin adjacent to left superior cervical ganglion 20. Device 40 is operated to produce electrical stimulation comprising a rectangular square pulse. The pulse is of msec duration, 50 Hz, and 10 volts, with a stimulus train duration of 20 msec. Alternatively, the pulse is of 0.1-3 msec duration, 25-75 Hz, and 5-15 volts, with a stimulus train duration of 10-30 msec.

Figure 3:
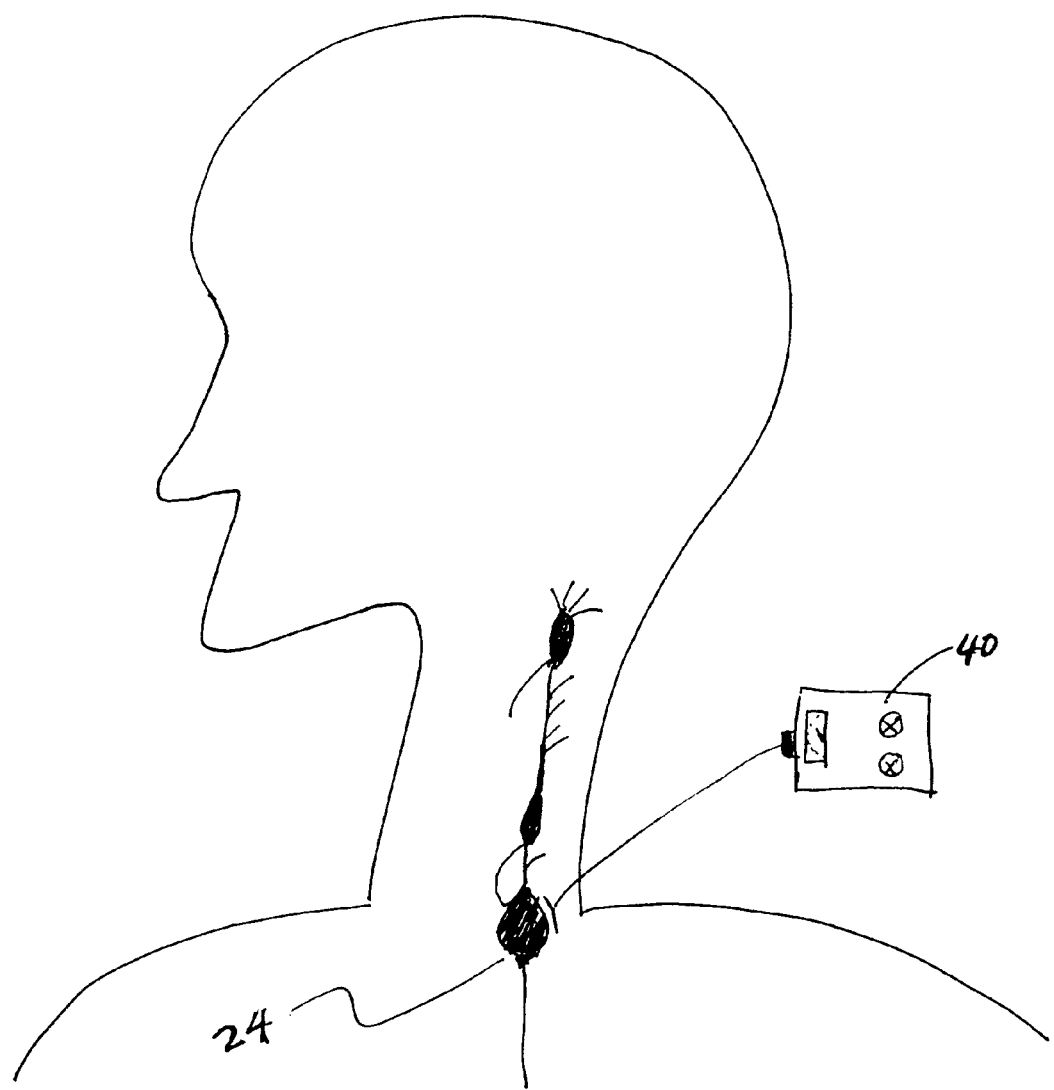
FIG. 3 depicts application of an electrical stimulation device to the left stellate ganglion to produce cerebral vasodilation.

In FIG. 3, transcutaneous electrical stimulating device 40 is applied to the skin of a patient at a region adjacent to left stellate ganglion 24. After measuring and determining the desired increase in cerebral blood flow, device 40 is operated according to the parameters given herein to stimulate or inhibit nerve impulses of the cervical sympathetic chain. In this manner, the electrical stimulation produces vasodilation in the cerebral vasculature, thereby increasing cerebral blood flow.

Figure 4:
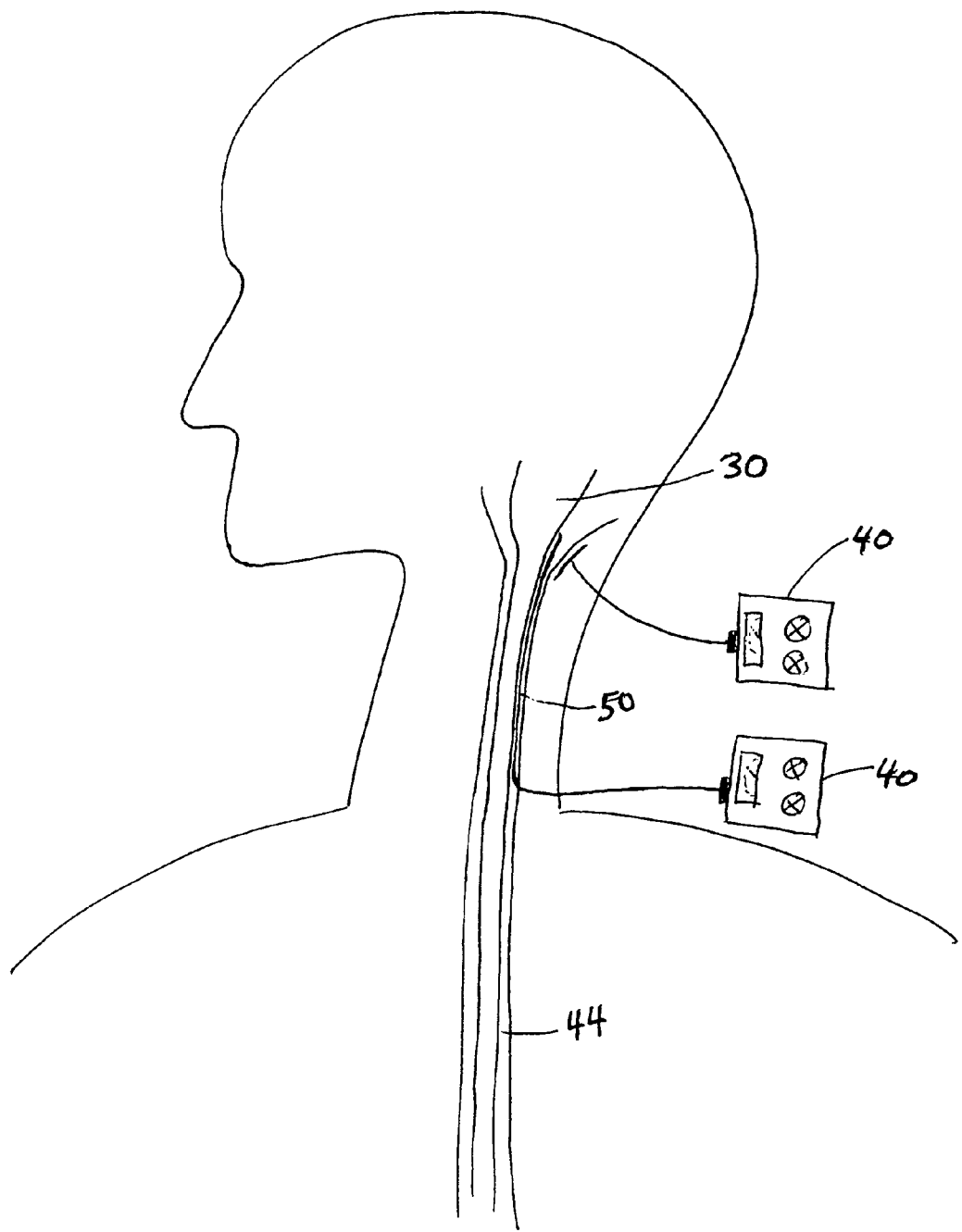
FIG. 4 depicts application of an electrical stimulation device to the skin of a patient at a region adjacent to the brainstem or through the subarachnoid space to stimulate the brainstem to produce cerebral vasodilation.

Since the sympathetic centers in the brainstem provide central regulation of peripheral sympathetic activity, activation of the brainstem also produces desirable vasodilatory effects on the cerebral vasculature, thereby increasing cerebral blood flow. Stimulation of the brain stem is achieved by applying transcutaneous electrical stimulation device 40 to the skin of a patient at a region adjacent to the brainstem (usually at the base of the skull) as shown in FIG. 4. Alternatively, catheter 50 is inserted into subarachnoid space 44 through cervical, thoracic, or lumbar puncture. Distal end 51 of catheter 50 is positioned adjacent brainstem 30 as shown in FIG. 4. The proximal end of catheter 50 is attached to electrical stimulating device 40. By operating device 40 according to the parameters given herein, sympathetic centers in brainstem 30 are stimulated or inhibited to produce a desired increase in cerebral blood flow, thereby minimizing cerebral ischemia in patients with stroke.

Figure 5:
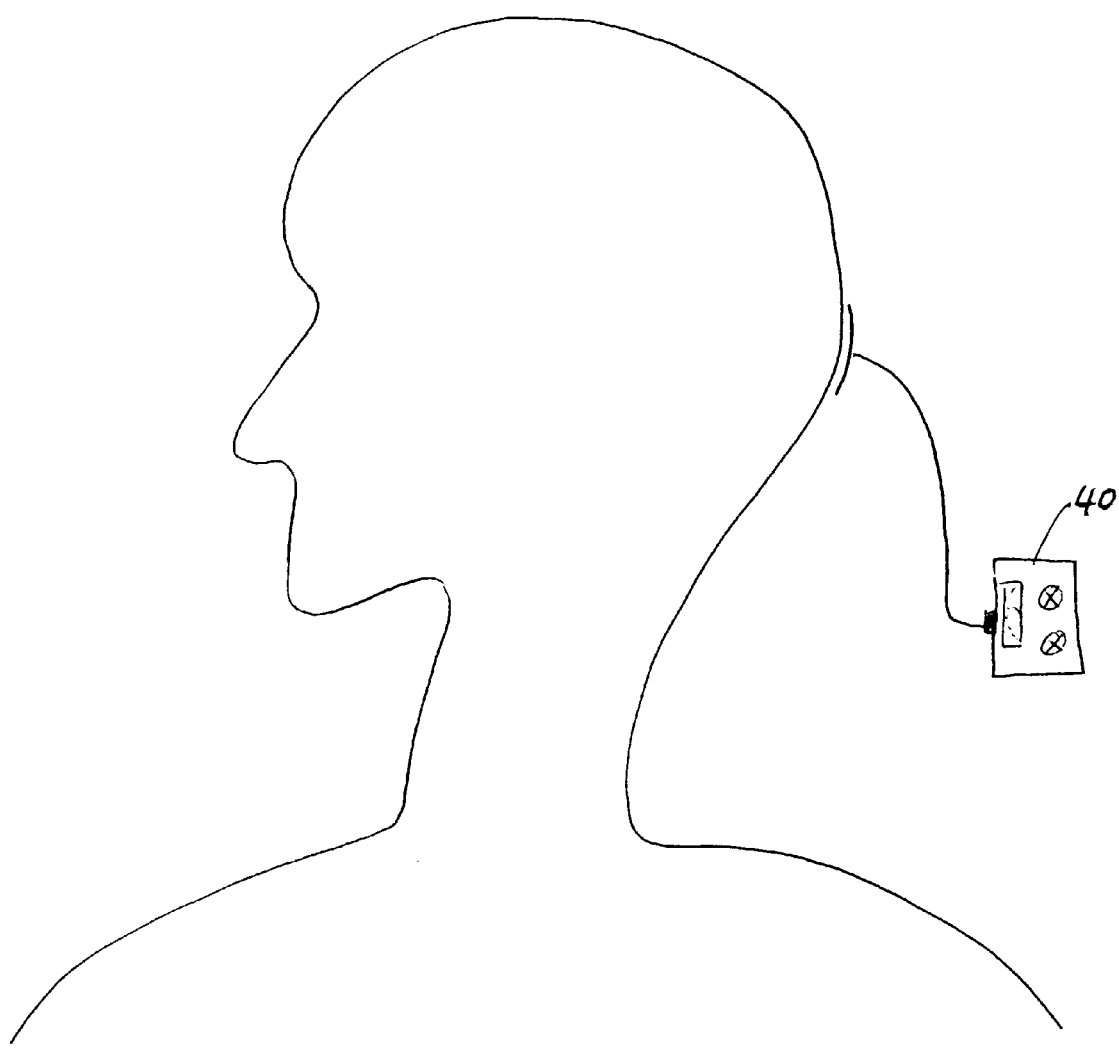
FIG. 5 depicts application of an electrical stimulation device to the head of a patient to produce cerebral vasodilation.

The brainstem sympathetic centers are regulated by many stimuli, including impulses coming from centers higher up in the brain, such as the cortex, limbic lobe, and the hypothalamus. Therefore, by applying electrical stimulating device 40 according to the parameters given herein to the head of the patient as shown in FIG. 5, sympathetic activity in the higher brain centers is inhibited, producing an increase in cerebral blood flow.

Figure 6:
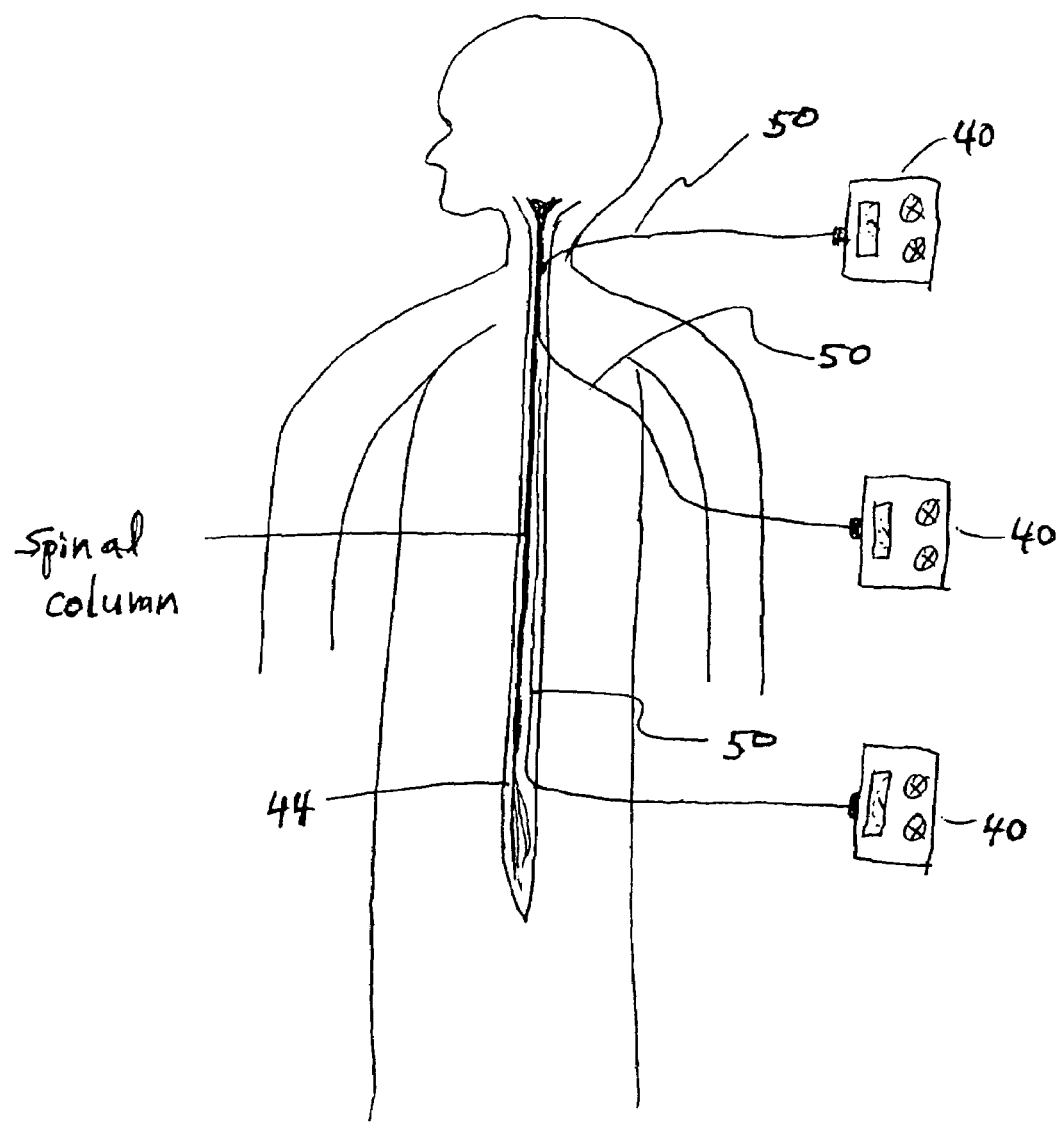
FIG. 6 depicts inserting a catheter carrying an electrical stimulation device in the subarachnoid space to stimulate the cervical sympathetic chain to produce cerebral vasodilation.

The cervical sympathetic ganglia receive their preganglionic fibers from the superior thoracic spinal nerves that originate from the spinal cord. Stimulation of the thoracic spinal nerves produces sympathetic inhibition of the impulses going to the sympathetic ganglion. In FIG. 6, catheter 50 is inserted between two low cervical vertebrae into subarachnoid space 44. The distal end of catheter 50 is positioned adjacent the superior thoracic spinal nerves whereas the proximal end of catheter 50 is attached to electrical stimulating device 40. Alternatively, catheter 50 is inserted between two high thoracic vertebrae into subarachnoid space 44. The distal end of catheter 50 is positioned adjacent the superior thoracic spinal nerves whereas the proximal end of catheter 50 is attached to electrical stimulating device 40. Alternatively, catheter 50 is inserted between two lumbar vertebrae into subarachnoid space 44. The distal end of catheter 50 is advanced and positioned adjacent the superior thoracic spinal nerves whereas the proximal end of catheter 50 is attached to electrical stimulating device 40. Device 40 is operated according to the parameters given herein to stimulate or inhibit nerve impulses of the cervical sympathetic chain, thereby producing cerebral vasodilation and cerebral blood flow.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for increasing cerebral blood flow in a patient, comprising the steps of:
    providing an elongate member having a proximal end, a distal end, and an electrical stimulating device mounted on the distal end of the elongate member;
    inserting the elongate member between lumbar vertebrae, low cervical vertebrae, or high thoracic vertebrae into the subarachnoid space;
    advancing the electrical stimulating device cephalad and positioning the electrical stimulating device adjacent the brain stem;
    measuring cerebral blood flow;
    operating the electrical stimulating device to stimulate or inhibit nerve impulses of the brain stem, thereby producing vasodilation in the cerebral vasculature, thereby increasing cerebral blood flow; and
    measuring cerebral blood flow after the step of operating the electrical stimulating device.

2. The method of claim 1, further comprising the step of determining the increase in cerebral blood flow produced by operating the electrical stimulating device.

3. The method of claim 1, wherein the electrical stimulating device is positioned at a region adjacent the medulla.

4. The method of claim 1, wherein the electrical stimulating device is a GRASS stimulator.

5. The method of claim 1, wherein the electrical stimulating device is operated to produce electrical stimulation comprising a rectangular square pulse.

6. The method of claim 1, wherein the electrical stimulating device is operated to produce electrical stimulation comprising a pulse of 1 msec duration, 50 Hz, and 10 volts, with a stimulus train duration of 20 msec.

7. The method of claim 1, wherein the electrical stimulating device is operated to produce electrical stimulation comprising a pulse of 0.1-3 msec duration, 25-75 Hz, and 5-15 volts, with a stimulus train duration of 10-30 msec.

* * * * *